(12) United States Patent
Zhang

(10) Patent No.: US 10,788,484 B2
(45) Date of Patent: Sep. 29, 2020

(54) APPARATUS AND METHOD FOR ABSOLUTE QUANTIFICATION OF BIOMARKERS FOR SOLID TUMOR DIAGNOSIS

(71) Applicant: QUANTICISION DIAGNOSTICS INC., Chapel Hill, NC (US)

(72) Inventor: Jiandi Zhang, Chapel Hill, NC (US)

(73) Assignee: QUANTICISION DIAGNOSTICS INC., Chapel Hill, NC (US)

( * ) Notice: Subject to any disclaimer, the term of this patent is extended or adjusted under 35 U.S.C. 154(b) by 112 days.

(21) Appl. No.: 16/022,259

(22) Filed: Jun. 28, 2018

(65) Prior Publication Data

US 2019/0004037 A1    Jan. 3, 2019

Related U.S. Application Data

(60) Provisional application No. 62/526,425, filed on Jun. 29, 2017.

(51) Int. Cl.
| | |
|---|---|
| *G01N 33/543* | (2006.01) |
| *G01N 33/68* | (2006.01) |
| *G01N 33/574* | (2006.01) |
| *G16H 50/20* | (2018.01) |

(52) U.S. Cl.
CPC ..... *G01N 33/54306* (2013.01); *G01N 33/574* (2013.01); *G01N 33/57484* (2013.01); *G01N 33/6893* (2013.01); *G01N 2800/52* (2013.01); *G16H 50/20* (2018.01)

(58) Field of Classification Search
None
See application file for complete search history.

(56) References Cited

U.S. PATENT DOCUMENTS

| | | |
|---|---|---|
| 2011/0251096 A1 | 10/2011 | Southern |
| 2012/0115138 A1 | 5/2012 | Deigner et al. |
| 2013/0178384 A1 | 7/2013 | Zhang |
| 2014/0227372 A1 | 8/2014 | Missiaglia et al. |

FOREIGN PATENT DOCUMENTS

WO    2017214068 A1    12/2017

OTHER PUBLICATIONS

Ura et al. (Int. J. Cancer 1992 50:57-63). (Year: 1992).*
Tan et al. (PLoSOne 2011 6:e18764). (Year: 2011).*
CoAA (Sui et al. Oncogene 2007 26:822-835) (Year: 2007).*
Guillemin et al. "Validation of a Dot-Blot quantitative technique for large scale analysis of beef tenderness biomarkers," J Physiol Pharmacol, Oct. 1, 2009 (Oct. 1, 2009), vol. 60, Suppl. 3, pp. 91-97.
Venugopal et al. "Quantitative proteomics for identifying biomarkers for Rabies," Clin Proteomics, Mar. 22, 2013 (Mar. 22, 2013), vol. 10, No. 3, pp. 1-13.
Tian et al. "Quantitative dot blot analysis (QDB), a versatile high throughput immunoblot method," Oncotarget, Apr. 19, 2017 (Apr. 19, 2017), vol. 8, No. 35, pp. 58553-58562.
International Searching Authority/US, "PCT International Search Report" for PCT/US2018/040075, dated Sep. 13, 2018.

* cited by examiner

*Primary Examiner* — Changhwa J Cheu
(74) *Attorney, Agent, or Firm* — Novick, Kim & Lee, PLLC; Allen Xue

(57) ABSTRACT

Provided is a method for quantitative analysis of a sample. The method includes steps of (a) providing a singular marker representative of one or more features of the sample, the sample comprising a population of individual units of the marker; (b) measuring the marker with dot blot analysis, wherein the quantitation result is an absolute amount of the marker's population of individual units in the sample, normalized by the sample volume or by the sample weight; and (c) obtaining an objective determination of the one or more features of the sample based on the quantitation result of the marker. Also disclosed is a reference database and a method to use the reference database for diagnosing cancer in a patient.

13 Claims, 5 Drawing Sheets

FIG. 1A
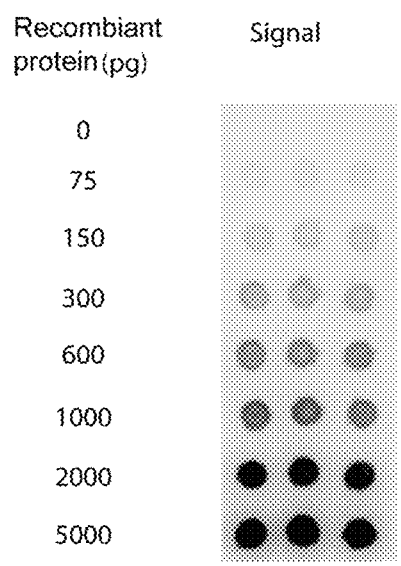
FIG. 1B
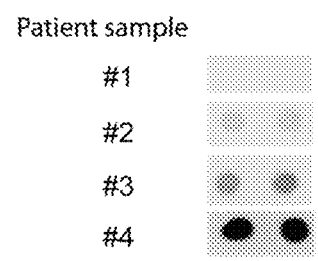
FIG. 1C
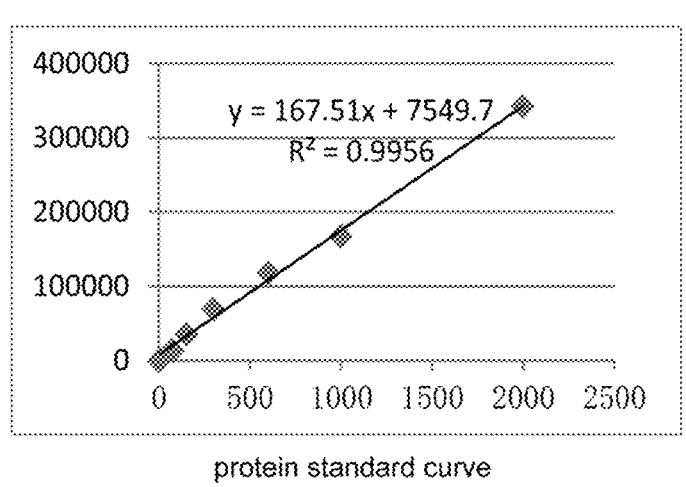
protein standard curve
FIG. 1D
Measured protein level
| | |
|---|---|
| #1 | 0 |
| #2 | 7.08 nmole/g |
| #3 | 0.92 nmole/g |
| #4 | 36.04 nmole/g |

APPARATUS AND METHOD FOR ABSOLUTE QUANTIFICATION OF BIOMARKERS FOR SOLID TUMOR DIAGNOSIS

CROSS-REFERENCE TO RELATED APPLICATIONS

This application is a U.S. nonprovisional patent application which claims the benefit of provisional application No. 62/526,425, filed on Jun. 29, 2017, the disclosure of which is hereby incorporated by reference. Further, U.S. application Ser. No. 14/721,205, filed on May 26, 2015, and U.S. application Ser. No. 15/433,586, filed on Feb. 15, 2017 (now U.S. Pat. No. 10,225,544), are also hereby incorporated by reference in their entireties for all purposes.

FIELD OF THE INVENTION

The present disclosure relates to methods and apparatus for quantification of biomarker at tissue level for diagnostics purpose using immunoblot method. Specifically, this disclosure provides methods and apparatus to measure the expression level of a biomarker using quantitative dot blot analysis (QDB), and when combined with a reference database, to provide diagnosis and prognosis for solid tumors.

BACKGROUND

Protein analysis is the basis of modern biological research. It centers on antigen-antibody interaction to measure levels of antigen of interest under various medical or experimental conditions. An antigen by definition is a foreign molecule that triggers the production of an antibody by the immune system when introduced into the body. The high specificity of the antibody against a specific antigen makes it a powerful tool in clinical, pharmaceutical and biomedical research.

An antigen includes, but not limited to a chemical compound, a peptide, a protein, an RNA, a DNA, a cell (proteins released in situ), or a virus particle (proteins released in situ). The molecule of antigen, as a whole or in part, may be introduced into a host animal, such as a donkey, a goat, or a rabbit to generate a large quantity of antibody against the introduced antigen of interest. Furthermore, the introduced antigen, or part of the antigen, may have more than one epitopes, thus may generate a corresponding number of antibodies against the antigen of interest.

A typical immunodetection process has three major steps. The first step is sample application, in which prepared samples containing an antigen of interest is first bound to a solid phase, such as nitrocellulose or PVDF membrane, multi-well plate with protein binding capacity, glass slide in immunohistochemistry analysis (IHC) or membrane at QDB plate, Zhang et al. "*Quantitative dot blot analysis (QDB), a versatile high throughput immunoblot method*" Oncotarget 2017 Vol. 8, page 58553-58562, which is incorporated by reference herein in its entirety. The second step is to form and label the antigen-antibody complex (i.e., immunocomplex) of interest. This step involves the sub-steps of blocking, incubation and washing. In the blocking sub-step, non-specific protein binding sites on the membrane are blocked using a blocking buffer to shield them from non-specific protein. In some case of IHC, slice on the glass slide needs to be further processed (de-paraffined and antigen retrieval) before the blocking buffer is applied. After blocking, the membrane is incubated in the incubation step with antibody against the antigen of interest to form membrane-bound antigen-antibody complex. The unbound antibodies are washed away. The antibody used herein is often commercially available as a pre-labelled antibody. One may also perform the labeling sub-step on site. In either case, the antibody shall be labeled, either directly with a reporter, e.g., a reporter enzyme, or indirectly labelled using a secondary antibody conjugated with a reporter.

The third step is detection. Signals emitted by the reporter enzyme are detected and recorded, which yield information related to the quantity or quality of the immunocomplex bound on the membrane.

Different methods of labeling the antibody in turn necessitate different corresponding detection methods. For example, the third step of detection may be a color reaction by visual inspection or chemiluminescence signals detectable through scanner, X-ray film or microplate reader, etc. The antibody may also be fluorescence-labeled and detected through scanner Multiple techniques of protein analysis are variations of this typical immunodetection process. These techniques include, but not limited to, Western blot analysis, Dot blot analysis, immunohistochemistry (IHC), Enzyme-linked immunosorbent assay (ELISA), reverse phase protein microarray (RPPM) and newly developed Quantitative Dot Blot analysis (QDB) and Zestern analysis.

In immunohistochemical analysis, the tissue is first processed either as paraffin-embedded block or as a frozen tissue, and is further sliced at certain thickness before the tissue slice is placed on a slide. Next, the slide is going through a typical immunodetection process to form immunocomplex between antigen of interest and detection antibody on the slide. The pre-labeled antibody is used to allow detection of antigen of interest on the slide by a pathologist with the aid of microscope. For slice from paraffin-embedded block, the slice needs to go through further steps to facilitate antigen-antibody interaction. These steps may include de-paraffin of the slice, and antigen retrieval step to expose the antigen for antigen-antibody interaction.

In clinical practice, IHC is widely used to detect any changes at protein level of a biomarker for diagnostic or prognostic purpose. A typical IHC report of a biomarker either expresses as "+" or "−", or it is further categorized as "0, 1+, 2+, 3+". For example, the expression level of one commonly used biomarker for breast cancer diagnosis, Human epidermal growth factor receptor 2 (Her2), is assessed using IHC to determine if Her2-dependent therapy should be included in the treatment plan. The IHC results are categorized into four groups: 0 and 1+, 2+, and 3+. 0 and 1+ group is considered as negative, 3+ is considered as positive while 2+ is considered as equivocal.

Attempts trying to unite the intensity of staining with the percentage of cells stained lead to scoring system including H score (or H index) developed to provide more informative detail about IHC analysis. In other cases, the intensity of the staining, for example, strong or weak and the percentages of the cells stained are both provided. For example, the results can be reported as (percentage, intensity). However, all these results are semi-quantitative in nature.

Although IHC provides valuable morphological information, and numerous efforts have been invested to standardize the analytical procedure, its result is still qualitative, affected by various factors including the process of treatment, the field of view and inter-observer variability. It is also rather challenging to adapt this technique into a high throughput format.

The uncertainty associated with IHC analysis consequently leads to significantly increased error in diagnosis. In fact, in Her2's case, there are as much as 30% inconsistency between IHC with Fluorescence In Situ Hybridization technique (FISH).

The categorized results of IHC analysis also makes it difficult for further data analysis. For example, while there are significant differences among individual patients with positive results, they are all considered in the same category in clinical practice. Thus, results from IHC analysis are unable to be used for extensive data analysis to provide more accurate, more predictive diagnosis or prognosis as we expected.

There have been several attempts to measure quantitatively the biomarker at tissue level with success. For example, Hermark assay, based on the proximity assay, was able to quantify Her2 levels at breast cancer tissues[4]. However, this technique measures the relative Her2 level among breast cancer patients.

In the meantime, the absolute Her2 level was achieved with SRM-MS technique. Using an isotope labeled protein standard, the absolute Her2 levels were measured, and a cutoff of 740 amole/µg was proposed based on the Receiving Operative Characteristics (ROC) analysis.

Nonetheless, these methods are complicated and labor intensive, not suitable for high throughput analysis of a large number of samples. The complex process also leads to significantly increased operating cost and efforts.

The recently developed QDB method, on the other hand, has been demonstrated suitable to process complex lysates prepared either from cells or tissues in a high throughput format. Introduction of a protein standard, either in the form of a recombinant protein, or a purified protein, conveniently translates this method into an absolute quantitative assay to measure the absolute content of a specific protein at cellular or tissue level.

In this invention, the effort was made to adopt QDB assay in measuring the expression level of a biomarker at tissue level for clinical use. In one application of current invention, the IHC assays currently available for diagnostics purpose can be converted into absolute quantitation assays with clear advantages of accurate, quantitative, objective, high throughput, and more comprehensive to aid clinical diagnosis or prognosis. The absolute values from QDB analyses can be further processed in large scale for data analysis to provide more predictive and accurate diagnosis and prognosis.

SUMMARY OF THE INVENTION

The present invention provides method to quantify the expression levels of biomarkers at tissue levels. The evaluation of biomarkers is quantitatively measured instead of categorized as in current prevailing methods.

Consequently, the present invention provides a continuous result to replace the current prevailing discrete result. Thus, the present invention opens more opportunities than the current prevailing method of IHC and FISH.

One aspect of the present invention relates to a method for quantitative analysis of a sample. The method includes steps of (a) providing a singular marker representative of one or more features of the sample, which contains a population of individual units of the marker; (b) measuring the marker with dot blot analysis, wherein the quantitation result is an absolute amount of the marker's population of individual units in the sample, normalized by the sample volume or by the sample weight; and (c) obtaining an objective determination of the one or more features of the sample based on the quantitation result of the marker.

The sample can be a tissue from a subject. In one embodiment of current invention, the tissue refers to a biopsy tissue. In another embodiment of current invention, the tissue refers to a frozen tissue. Yet in another embodiment of current invention, the tissue refers to a Formalin Fixed specimen, and yet in another embodiment of current invention, the tissue refers to a Formalin Fixed Paraffin Embedded specimen (FFPE specimen).

The subject can be a patient. Specifically, the subject can be a cancer patient.

On the other hand, the step (b) of the above method can include measuring the marker with quantitative dot blot (QDB) analysis. More specifically, the step (b) can include: (b1) incubating the sample with a solution containing a binding agent, which is capable of specifically binding to an individual unit of the marker and is capable of being quantified by the dot blot analysis; and (b2) measuring the marker through QDB analysis of the binding agent.

The binding agent can be capable of being assayed based on antibody-antigen interaction including immunohistochemistry. Moreover, the binding agent can be capable of being assayed in flow cytometry.

Preferably, the marker is a protein marker and the binding agent is an antibody. Further, the antibody can be an analyte specific regent (ASR) antibody, and it can also be an in vitro diagnostics (IVD) antibody.

Additionally, the above-described method further includes step (d) of evaluating the patient based on the quantitative result of the marker. Particularly, step (d) includes diagnosis and prognosis of a cancer for the patient. Examples of diagnosis and prognosis of a cancer for the patient include disease-free survival, overall survival, Hazard Ratio (HR), or treatment prediction for the cancer.

The quantitatively measured biomarker level disclosed in this invention can be categorized based on mathematical analysis of available information to facilitate the comparison from this invention to the current prevailing method, and to help better explore the clinical significance of the absolute level of a biomarker.

One embodiment of current invention is through immunoblot analysis. The expression level of a biomarker can be measured using an antibody-based method.

By defining the linear range of the antibody-based method, the absolute level of a biomarker can be measured with a protein standard in the same measurement.

In one embodiment of current invention, dot blot method can be used to achieve the absolute level of a biomarker at tissue.

Purified or recombinant protein is used to establish a protein standard curve using image-based dot blot analysis. The image is converted into number through image capture and analysis.

The captured signal is used to establish a protein standard curve.

Total protein extracted from FFPE block can be used in dot blot analysis, and the captured signal can be converted into absolute biomarker level using the referenced standard curved described above.

In one embodiment of current invention, the Quantitative Dot Blot analysis (QDB) method can be used to achieve the absolute level of a biomarker at tissue level.

The protein expression level of a biomarker can be measured relatively through immunoblot assay including QDB method in the absence of a protein standard. As long as the process of analysis is well controlled (e.g., with the positive and negative controls), it provides informative result for reference.

In QDB analysis, the absolute level of a biomarker can be measured using a validated detection antibody. There is no limitation of methods to validate the detection antibody. The antibody can be validated through Western blot analysis, or it can be validated based on prior experience. In one embodiment of current invention, a well-accepted antibody for immunohistochemistry can be used directly in QDB analysis. For example, ASR or IVD antibodies can be used in QDB analysis. These antibodies include, but not limited to, EP3 and 4B5 clones for HER2 protein, MIB1 for ki67 and SP1 for Estrogen Receptor (ER). Likewise, a detection antibody for other antibody-based assay, including, but not limiting, flow cytometry, can be used in QDB analysis.

A detection antibody (antibody A) can be validated through comparative study with an existing detection antibody (antibody B). When more than one sample are analyzed with both antibody A and antibody B with similar result, antibody A can be considered validated Sample for QDB analysis can be prepared from frozen tissue or from a formalin-fixed tissue or from a formalin-fixed-paraffin-embedded tissue block (FFPE block). It can also be prepared from tissues preserved in other format as long as the antigen-antibody interaction is allows to happen with the sample.

The absolute level of a biomarker from more than one sample can be combined with relevant clinical information to setup a protein database (AKA, QDB database). Mathematical analysis of QDB database provides information for medical use. For example, the putative association between absolute level of a biomarker and the disease free survival (DFS) can be explored to provide predictive clinical prognosis for a patient.

These and other embodiments of the present invention rely at least in part upon the finding that the absolute nature of the QDB analysis allows for combining results from more than one source for analysis. The continued addition of new information from QDB analysis allows growing of a QDB database. Information obtained through analysis of a QDB database provides diagnosis or prognosis for a patient.

Protein can be extracted in non-denatured form, or it can be further denatured through heating and/or reducing reagent. The non-denatured form should be taken in their broadest context. It can be in native form; or it may refer a state where the antigen is either not exposed to reducing agents (e.g., Dithiothreitol (DTT) or β-mercaptoethanol) or not exposed to a sufficient amount of reducing reagent to completely denature the antigen.

In one embodiment of the current invention, an antigen with predetermined amount can be included as operational control to ensure the consistency of experiment. The absolute level of the antigen needs to be measured each time, and only when the measured result is within the certain range of the pre-determined amount before the overall experiment can be accepted as valid.

The QDB analysis can also be performed using the same lysate with more than one antibody against the same biomarker. These antibodies can direct against the same epitope, or against different epitopes of the biomarker. A cutoff reference can be developed for these antibodies respectively, and the sample can be determined either as positive or negative in reference to these cutoff reference values. Samples agreed by all antibodies can be accepted as positive or negative, and those with disagreeable results can be assigned as equivocal.

In one embodiment of current invention, the absolute levels of more than one biomarker can be quantified using the same sample, and the combination of these information together with relevant clinical information, including, but not limited to, the disease free survival, the overall survival, the hazard ratio, the side response, the age, the progression stage of the disease, can be used to find a pattern, and this pattern can be used for diagnosis and prognosis purpose.

In one embodiment of current invention, the absolute level of a biomarker can be measured with more than one antibody, and the absolute levels of a biomarker based on each antibody respectively over relevant clinical information, including, but not limited to, the disease free survival, the overall survival, the side response, the hazard ratio, the age, the progression stage of the disease, can be used to find a pattern respectively, and individual pattern from different antibodies can be used to provide antibody-specific information for diagnosis and prognosis purpose.

Another aspect of the present invention relates to a reference database for diagnosing cancer in a patient based on quantitative analysis of a marker in a biopsy sample from the patient. The reference database includes a plurality of reference profiles. each of the plurality of the reference profile is prepared by steps of: (a) providing a biopsy sample from a cancer patient with a known diagnosis; (b) measuring said marker with dot blot analysis for the biopsy sample, wherein the quantitation result is an absolute amount of said marker in the biopsy sample, normalized by the biopsy sample volume or by the biopsy sample weight; and (c) associating the quantitation result with the known diagnosis of the cancer patient thereby obtaining a reference profile.

The step (b) described above can include (b1) incubating the biopsy sample with a solution containing a binding agent that specifically binding to said marker; and (b2) measuring said marker through QDB analysis of the binding agent.

In the above reference database, preferably the marker is a protein marker and the binding agent is an antibody. Advantageously, the reference database is stored in a computational memory chip.

Yet another aspect of the present invention is directed at a method for diagnosing cancer in a patient. The method includes steps of (i) providing a reference database described above, (ii) obtaining a biopsy sample from the patient; (iii) measuring the marker used in the reference database in the biopsy sample from patient with dot blot analysis, the measured result being an absolute amount of the marker in the biopsy sample; (iv) comparing the measured result of the marker with that of each reference profile stored in the reference database; and (v) identifying a reference profile in the reference database that has the best match and outputting the known diagnosis associated with the identified reference profile.

In the above method, the cancer being diagnosed is solid tumor.

Still another aspect of the present invention relates to an apparatus for diagnosing cancer in a patient. The apparatus contains the reference database just described.

Yet another aspect of the present invention relates to a kit for diagnosing cancer in a patient. The kit contains the above reference database. Alternatively, the kit contains a unit configured to access online the above reference database.

The details of the invention are set forth in the drawing and the description below. Other features, objects, and advantages of the invention will be apparent to those persons skilled in the art upon reading the drawing and the description, as well as from the appended claims.

BRIEF DESCRIPTION OF THE DRAWINGS

FIGS. 1A-1D: Measuring the absolute her2 level with EP3 antibody using dot blot analysis. Purified her2 protein was used to define a dose curve, and the captured image was converted into number using ImageQuant from Li-Cor. A dose curve was established, and used to convert the captured dot blot image from patient samples into absolute Her2 level among these patients.

DETAILED DESCRIPTION

Figure 2A:
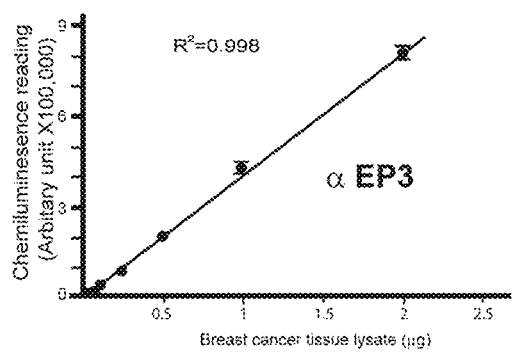
FIGS. 2A-2H defining the linear range of three known antibodies for IHC analyses of Her2, Ki67 and ER in QDB analysis. Recombinant proteins of Her2, Ki67 and ER were used as protein standard. The dose response curves were established using QDB analyses with these antibodies respectively.

Before the present methods are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

Unless otherwise defined in this disclosure, all technical and scientific terms used herein have the same meaning as is commonly understood by one of skills in the art to which this disclosure belongs.

The subject methods are useful primarily for diagnostic purposes. Thus, as used herein, the terms "determining," "measuring," and "assessing," and "assaying" are used interchangeably and include both quantitative and qualitative determinations. These terms can also refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

Whenever applicable, "quantitative" assays in general provide information on the amount of an analyte in a sample relative to a reference (control), and are usually reported continuously numerical, where a "zero" value can be assigned where the analyte is below the limit of detection. "Semi-quantitative" assays yielding an approximation of the quantity or amount of a substance; between a qualitative and a quantitative result, where a "zero" value can be assigned where the analyte is below the limit of detection.

The term "diagnosis" is used herein to refer to the identification of a molecular or pathological state, disease or condition, such as the identification of a molecular subtype of breast cancer or other type of cancer.

The term "prognosis" is used herein to refer to the prediction of the likelihood of cancer-attributable death or progression, including recurrence, metastatic spread, and drug resistance, of a neoplastic disease, such as breast cancer.

The term "predicative" is used here to refer to the prediction of the outcome of therapeutic intervention.

The terms "subject," "host," "patient," and "individual" are used interchangeably herein to refer to any mammalian subject for whom diagnosis or therapy is desired, particularly humans.

As used herein, the term "unit," in the context of an antibody-based essay, refers to an epitope of a target protein. In a more general setting, "unit" could represent a hybridizing region recognized by a binding agent.

Quantitation by QDB

The quantitatively measurement of the protein expression level of a biomarker can be achieved at tissue level using immunoblot method. The immunoblot method is to be considered to its broadest context. As long as the analytical process is antibody-based, and a solid phase is involved in the process, it can be considered as immunoblot analysis. The solid phase includes, but not limited to, a membrane, the ELISA plate, the QDB plate (AKA, the plate used in QDB analysis).

There is no limitation to how the antibody is validated. The antibody can be validated using Western blot analysis when linear epitope is used; it can also be validated based on prior experience. For example, a lot of antibodies have been used in clinical diagnosis and prognosis. These antibodies include, but not limited to ASR or IVD antibodies, and other clinically accepted antibody for immunohistochemistry or flow cytometry analysis. All these antibodies can be used in QDB analysis without further validation.

A detection antibody can also be validated in reference to a known detection antibody. In one embodiment of current invention, a detection antibody is used to analyze more than one sample, and the results are compared with those from a known antibody. For example, 4B5 clone from Roche for HER2 protein. When the concordance is beyond certain value, this antibody can be considered as a validated antibody.

In one embodiment of current invention, the expression level of a biomarker is measured with a typical immunoblot method. This method includes, but not limited to two features, including 1) a validated antibody and 2), A dose curve can be established using a protein standard.

In one embodiment of current invention, the expression level of a biomarker is measured with a typical immunoblot method. This method includes, but not limited to three features, including 1) a validated antibody and 2) a dose curve can be established using a protein standard, and 3) the immunocomplex on the membrane is individual quantified, without the interference from neighboring unit during the detection process.

In one embodiment of current invention, a reference sample can be included in the experiment. The reference sample is processed with a sample of interest in the same immunoblot analysis. The result of the reference sample is compared with that of sample of interest to determine if the sample of interest is positive when the result of sample of interest is above that of reference sample, or vice versa.

In another embodiment of current invention, more than one reference sample are included in the experiment. The reference samples are processed together with sample of interest in the same immunoblot analysis. The results of reference samples are used to define a ranked order, and the result of sample of interest is determined in reference to those of reference samples. For example, if reference sample 1 and reference sample 2 are included to define the upper limit of 1+ and 2+, and the result from sample of interest is between those of reference sample 1+ and reference sample 2+, the sample of interest is assigned as 2+.

In one embodiment of current invention, the expression level of a biomarker is measured quantitatively using dot blot method. The Dot blot analysis includes, but not limited to, features including a) a validated antibody; b), defined linear range when the antibody is used to analyze one type of sample, and c), the immunocomplex on the membrane is detected as an image, and d), the conversion of image into a number.

In another embodiment of current invention, the expression level of a biomarker is measured quantitatively using QDB method. The QDB analysis includes, but not limited to, features including a) a validated antibody; b), defined linear range when the antibody is used to analyze one type of sample; and c), the immunocomplex on the membrane is individual quantified, without the interference from neighboring unit during the detection process.

The categorized results in current prevailing form of IHC should be considered in its broadest context. These results can be binary (positive or negative), or ranked (0, 1+, 2+, 3+ or strong, medium or weak), or by percentage, or in combination of all the above. Several scoring systems for IHC, including H score, is still considered as categorized results, as the result is discrete in nature The result from the method disclosed in this invention is a continuous data. Although this data can be converted into a categorized result as in prevailing IHC system to facilitate the comparison and understanding of the clinical significance of the result from this invention, this conversion is based on a cutoff reference derived from mathematical analysis, and the category where it belongs to can vary in reference to difference cutoff reference. In one embodiment of current invention, the measured Her2 levels in breast cancer tissue can be used for statistical analysis, and a cutoff value can be derived from Receiver Operative Characteristic analysis (ROC) based on IHC results, and the absolute level in breast cancer tissue can be assigned as either "positive" or "negative" in reference to the derived cutoff value from ROC analysis, with absolute Her2 level above the cutoff value as positive, and verse versa.

Absolute Measurement

The result from current invention can be relative, or, in combination with a protein standard, to be absolute. The terms "relative" and "absolute," referring to two ways to take a measurement, should be taken into their broadest context. While relative measurement is measuring one thing compared to another thing, absolute measurement is measuring things in known amounts with standard units. Perhaps, the most significant difference between these two measurements lies in each's applicable scope. A relative result is only meaningful under the same experimental setting, while an absolute result should be comparable across a number of different analyses, even analyses taken at vastly separate places or times.

Accordingly, the absolute measurement used herein is achieved with the inclusion of a protein standard. This protein standard should be taken into its broadest context. It refers to an antigen of pre-determined amount, or one antigen of more than one pre-determined amount. It includes, but not limited to, the amount pre-determined by weight, by the percentage, by the volume, by the number of molecules (for example, the mole), or a combination of any two or more of above. It can be in pure form, or it can be in a mixture. It can be in native form, or it can be in non-denatured form, or it is in denatured form. In this disclosure, the non-denatured form can be considered as any form between native form and denatured form.

Biomarkers

A "sample" or "patient sample" or "biological sample," which is used interchangeably herein, generally refers to a sample which may be tested for a particular molecule, preferably a specific marker molecule associated with a biological signature, such as a biomarker shown in the paragraph below. Samples may include, but are not limited to, peripheral blood cells, CNS fluids, serum, plasma, buccal swabs, urine, saliva, tears, pleural fluid and the like. A sample used in the present invention generally refers to a tissue.

The term "marker" or "biomarker" here is to be defined at its broadest context. A "marker" or "biomarker," which is used interchangeably herein, generally refer to an organic biomolecule (e.g., a polypeptide) which is differentially present in a sample taken from a subject of one phenotypic status (e.g., having a disease) as compared with that from another phenotypic status (e.g., not having the disease or having a different disease). A biomarker is thus often established if differentially present between two different phenotypic statuses, when the mean or median level of the biomarker in a first phenotypic status relative to a second phenotypic status is calculated to represent statistically significant differences.

In the present invention, the biomarker is protein molecule measurable related with a biological or a disease state. It can be well established diagnostic biomarkers (for example, a diagnostic biomarker for IHC), or it can be biomarkers newly identified for in vitro diagnostics.

In one embodiment of present invention, the biomarker is used for diagnosis of solid tumor.

The known biomarkers for diagnostics include, but not limited to ACTH, ACTIN, ADENOVIRUS, AFP, ALK-1, AMYLOID A, ANDROGEN RECEPTOR, ANNEXIN, ARGINASE-1, BAP1, B-AMYLOID, BCL-1, BCL-2, BCL-6, BEREP4, Beta-Catenin, BOB1, BRACHYURY, BRST-2, C3d, C4d, CALCITONIN, CALDESMON, CALPONIN, CALRETININ, CD14, CD117, CD117, BM, CD123, CD138, CD15, CD163, CD1a, CD2, CD20, CD21, CD23, CD25, CD3, CD30, CD31, CD33, CD34, CD34, BM, CD38, CD4, CD43, CD45RA, CD45RB, CD45RO, CD5, CD56, CD57, CD61, CD68, CD7, CD79a, CD8, CD99, CDX2, CEAm, CEAp, Chromogranin, Chymotrypsin, Claudin 3, Claudin 4, CK MIX, CK20, CK34BE12, CK5/6, CK7, CK19, CKAE1/AE3, CKCAM5.2, CMV, c-Myc, CXCL13, CYCLIN D3, D2-40, DBA-44, Desmin, DOG-1, EBV, LMP, E-Cadherin, EGFR, EMA, EMA-Perineurioma, ER, ERG, Factor 13a, Factor 8, FOXP1, FSH, GALECTIN-3, Gastrin, GATA-3, GFAP, GH, Glucagon, Glut1, Glutamine synthetase, Glypican-3, GPC, GRANZYME, H. pylori, HBC, HBS, hCG, HepPar 1, Her2neu, HGAL, HHV-8, HMB-45, HPL, HSV, IDH1, IgA, IgD, IgG, IgG4, IgM, Inhibin, INI, Insulin, ISH EBV, ISH KAPPA, ISH LAMBDA, KAPPA, KBA62, KI67, Lambda, LANGERIN, LAT, LEF1, LH, LM02, LYSOZYME, MAP-2, MCT, MELAN A, MITF, MLH1, MNDA, MOC-31, MPO, MSH2, MSH6, MUC2, MUC5AC, MUM1, Myogenin, Napsin A, NB84, NEU N, Neurofilament, NKI/C3, NKX3.1, NPM, NSE, NUT, 2-Oct, Oct-3/4, p16, p53, p57, p63, Parvovirus, PAX-2, PAX-5, PAX8, PCSK9, PD-1, Perforin, PHH3, PHLDA1, PIN4, PLAP, PMS2, PR, PRAP, Prolactin, Prox1, PSA, RNA, S100, S100P, SALL4, SF-1, SMA, SMMS, Somatostatin, SOX-10, SOX11, SCAP, S1P, SREBP, Spirochetes, STATE, SV40, SYNAP, Tamm-Horsfall, T-bet, TCL-1, TCR, TCR, Gamma, TdT, THYRO, TIA-1, TOXO, Transthyretin, TRAP, TSH, TTF1, Tyrosinase, Vimentin, WT1, WT1 (C-19), ZAP70.

This method can be adopted to analyze the antigen in fresh tissue, or it could be used to analyze antigen in formalin fixed paraffin embedded block (FFPE). The antigen can be extracted from the tissue or FFPE by any method as long as the antigen from extraction process allows the process of antibody-antigen interaction to happen. For antigen in FFPE block, the slice needs to be de-paraffined with and without the antigen retrieval step to facilitate antigen-antibody interaction.

REFERENCE DATABASE

The QDB results from more than one sample of interest, together with their matching clinical information, can be used to setup a database for mathematical analysis (AKA, QDB database). A reference database can thus be built for diagnostic purposes.

The terms "reference" and "control" are used interchangeably to refer to a known value or set of known values against which an observed value may be compared. The known value represents an understood correlation between two parameters, e.g., a level of expression of a marker and its associated phenotype. As used herein, the known value constitute a reference profile in a reference database.

Accordingly, a reference database can be prepared storing a number of reference profiles for diagnostic purpose, each recording a marker expression level of a sample obtained from a subject with either a known diagnosis or known clinical outcome after therapy.

In one embodiment, the present invention also includes a method of determining a patient profile that best matches one or more reference profiles in a reference database. The method includes steps of (a) comparing, on a suitably programmed computer, the level of expression of a marker in a sample from a patient with reference profiles in a reference database to determine a measure of similarity between the patient profile and each of the reference profiles; (b) identifying, on a suitably programmed computer, a reference profile in a reference database that best matches the patient profile based on a maximum similarity among the measures of similarity determined in step (a); and (c) outputting to a user interface device, a computer readable storage medium, or a local or remote computer system; or displaying, the maximum similarity or the associated phenotype of the reference profile in the reference database that best matches the patient profile.

Absolute Value-Based Diagnostic Method

The putative association between the expression level of a biomarker and a clinical trait is explored using a mathematical method to analyze the information from a QDB database. The examples include, but not limited to, the relative expression level of HER2 with the disease free survival of the patient. The predicative value of Ki67 in treating stomach cancer patients. This information may provide prognosis for other patient in the same analysis.

As pointed out above, diagnostic tests used in clinical practice often rely on a single analyte, and therefore do not capture the value of its potentially intrinsic correlations with other parameters, including some clinical readings. Moreover, diagnostic tests are frequently not quantitative, relying on immunohistochemistry, which often yields different results in different laboratories, in part because the reagents are not standardized, and in part because the interpretations are subjective and cannot be easily quantified.

When the protein standard is included in the QDB analysis, the absolute level of a biomarker can be achieved, greatly facilitating benchmarking across different clinical laboratories. The QDB results from more than one sample of interest, together with their matching clinical information, can be used to setup a QDB database for mathematical analysis. The putative association between the absolute level of a biomarker and a clinical trait is explored using a mathematical method. The examples include, but not limited to, the absolute expression level of HER2 with the disease free survival of the patient. This information may provide diagnosis and prognosis for a patient in the future when the absolute level of the biomarker is measured.

The absolute results from more than one QDB analysis can be combined together to increase the size of the database for mathematical analysis. The putative association between the absolute level of a biomarker and a clinical trait is explored using a mathematical method. The examples include, but not limited to, the absolute expression level of HER2 with the disease free survival of the patient, or the predicative value of Ki67 in treating stomach cancer patient. This information may provide prognosis and diagnosis for a patient with known absolute level of a biomarker.

The absolute level of more than one biomarker can be measured using a sample of interest. These results, together with the clinical information of the patient of interest, can be used to setup a QDB reference database for mathematical analysis to provide diagnosis and prognosis to a patient when the absolute levels of these biomarkers are measured. Reference profiles can be obtained, each carrying the absolute level of biomarker for a patience with either a known diagnosis or known clinical outcome after therapy. Later for a new patient, his or her absolute level of the biomarkers can be determined and compared with those in the reference database. A match with the absolute level of a stored reference profile can be indicative of the associated diagnosis or prognosis for therapy for the new patient.

The clinical trait is to be considered in its broadest context. The trait may include, but not limited to, age, sex, blood pressure, glucose level, cancer stage, hazard ratio, disease free survival, or any information relevant to the diagnosis, prevention, treatment of the patient.

Another substantial advantage comes from the diagnostic method of the present invention. Specifically, the method can also be utilized for screening patients prior to entry into a clinical trial. A major impediment to cancer therapeutic trials aimed at personalized treatment is the lack of biomarkers available for stratifying the patients. The validation of an absolute value-based screening tool for cancer patients could significantly reduce the costs of such trials by using a single standard and refining the study entry process. With reduced costs for identification and screening of patients, the new methods for screening of the present invention facilitate recruitment, screening, and/or selection of patients from a broader range of populations and/or clinic settings, thereby offering underserved patient populations the opportunity to engage in clinical trials, which has been a major limitation to the majority of previously conducted trials in oncology.

Moreover, today's oncologists frequently have a number of treatment options available to them, including those labeled as "standard of care," and other drugs that do not carry such a label yet exhibited efficacy in certain types of cancer patients. Likelihood of good treatment outcome can be maximized if patients could be assigned to their optimal cancer treatment options as quickly as possible following diagnosis. The method of the present invention fulfills these needs by providing an enabling tool.

The absolute level of a biomarker can be measured with QDB analysis, or it may be measured with other method in addition to QDB analysis. In one embodiment of current invention, the absolute level of a sample of interest is verified with QDB analysis.

The absolute level of a biomarker for setting up a QDB database can be measured with QDB analysis, or it can be verified with QDB analysis. A QDB database should be considered in its broadest context. A QDB database includes at least one sample of interest with the absolute level of one biomarker measured or verified with QDB analysis.

The absolute level of a biomarker can be measured using more than one antibody. These antibodies can be against the same epitope, or they can be against different epitope of the biomarker. The absolute levels from these antibodies may be the same, or they are different from each other. When the absolute levels are different from each other using different antibodies, they should be specified with the antibody used, and be processed individually for diagnosis and prognosis purpose.

In one embodiment of current invention, when more than one detection antibody are used to measure the absolute level of a biomarker in a sample, If the diagnosis or prognosis is the same from these antibodies, the diagnosis or prognosis is considered as valid. If the diagnosis or prognosis is in disagreement, the diagnosis or prognosis is considered as "equivocal", which requires further verification.

Any antibody used for antigen-antibody interaction can be used for QDB analysis as long as it is validated as specific to the antigen of interest. In one embodiment of current invention, the antibody is monoclonal. In yet another embodiment of current invention, the antibody is polyclonal.

In one embodiment of current invention, an antibody for immunohistochemistry can be used for QDB analysis using tissue or a cell from a human or an animal.

In one embodiment of current invention, an antibody for flow cytometry can be used for QDB analysis using tissue or a cell from a human or an animal.

In yet another embodiment of current invention, an antibody for antigen-antibody based assay can be used for QDB analysis using tissue or a cell from a human or an animal.

In one embodiment of current invention, an antibody for a biomarker for QDB analysis of a sample can be labeled with fluorescence dye detectable at one wavelength, while another antibody for another biomarker for QDB analysis of the same sample can be labeled with fluorescence day detectable at another wavelength can be used simultaneously to analyze both biomarkers in the same sample.

In another embodiment of current invention, an antibody for a biomarker for QDB analysis of a sample can be labeled with one isotope, while another antibody for another biomarker for QDB analysis of the same sample can be labeled with another isotope can be used simultaneously to analyze both biomarkers in the same sample. In yet another embodiment of current invention, an antibody for a biomarker for QDB analysis of a sample can be labeled in one method, for example, with Horseradish peroxide (HRP); while another antibody for another biomarker for QDB analysis of the same sample can be labeled with a florescent dye to allow simultaneously measurement of two biomarkers in the same sample.

As used herein "reporter enzyme" is to be taken in its broadest context. A reporter enzyme can be any modification of the antibody in immunodetection assay with the purpose to aid the detection of the antibody. For example, a report enzyme can be, but not limited to, antibody directly labeled with radioactive isotope like Iodide 125, or reporter enzymes like alkaline phosphatase or horseradish peroxidase, or with a fluorescence day. The detection of the amount of reporter enzymes associated with antibody is through the formation of a detectable product as the readout of the amount of reporter enzymes in the detection reaction. The product can be radioactive, luminescent, fluorescent, or a product with characteristic absorbance or reflection spectrum in the visible or outside the visible range. When a complement is used to detect the bound antigen-antibody complex, it may either be labeled in any one of the above ways, or be detected in turn by a specific anti-complement antibody.

A report enzyme can be, but not limited to, antibody indirectly labeled with radioactive isotope like Iodide 125, or reporter enzymes like alkaline phosphatase or horseradish peroxide. Antibody can be, but not limited to, indirectly labeled through a secondary antibody, and the secondary antibody is directly or indirectly labeled with radioactive isotope like Iodide 125, or reporter enzymes like alkaline phosphatase or horseradish peroxide. In one embodiment, the secondary antibody is labeled with biotin, and indirectly further labeled with a horseradish peroxide through a streptavidin molecule.

As used herein "antigen" and an "antibody" are to be taken in their broadest context. An "antigen" can be a molecule, a cell, a virus, or a particle. The term "antigen" may be used to refer to a chemical compound, a peptide, a protein, an RNA, a DNA, a cell (proteins released in situ), or a virus particle (proteins released in situ) or any molecules that may evoke the production of one or more antibodies by a host animal, including human. An antigen may also be a product comprising any two or more of the molecules or moieties crosslinked together. An antigen can exists either in a pure form, or it can exist in a mixture. An antigen can be in a modified form (e.g., modified by a chemicals) or be in an unmodified form.

Reference herein to an "antibody" is to be taken in its broadest context. An "antibody" is a polypeptide that binds to "an antigen". An antibody includes, but is not limited to, a traditional antibody, a fragment of a traditional antibody containing an antigen binding site, a recombinant antibody containing an antigen binding site, a protein which binds to an antigen, and a product that comprises of crosslinking any two or more of the above. An antibody can exist either in a pure form, or in a mixture. An antibody can be in a modified form (e.g., modified by a chemical) or be an unmodified form.

"Solid tumor" is to be considered in its broadest term. A solid tumor refers to any tissue, cancer or non-cancer, which is connected at cellular level, and not existing as a single cell. It includes, but not limited to, breast cancer, prostate cancer, bladder cancer, stomach cancer, kidney cancer, Melanoma of skin, Cervix uteri cancer, head and neck cancer, brain cancer, thyroid cancer lung cancer, liver cancer, pancreatic cancer, and colorectal cancer.

It is to be understood that the exemplary embodiments described herein are that for presently preferred embodiments and thus should be considered in a descriptive sense only and not for purposes of limitation. Descriptions of features or aspects within each embodiment should typically be considered as available for other similar features or aspects in other embodiments.

Further, Examples put forth are not intended to represent that the experiments below are all or the only experiments performed. Efforts have been made to ensure accuracy with respect to numbers used (e.g., amounts, temperature, etc.) but some experimental errors and deviations should be accounted for.

Materials and Methods

Human Subjects and Human Cell Lines

Both Frozen tissues and formalin fixed paraffin embedded (FFPE) slices were obtained from local hospitals together with their clinical information including IHC scores (0, 1+, 2+ or 3+). Some of them were with FISH results. MCF-7 and BT-474 cell lines were purchased from the Cell Bank of Chinese Academy of Sciences (Shanghai, China), and lysates prepared from these two cell lines were used as HER2 negative and positive controls.

General Reagents.

All general reagents used for cell culture were purchased from Thermo Fisher Scientifics (Waltham, Mass., USA) including cell culture medium and culture dishes. The protease inhibitors were purchased from Sigma Aldrich (St. Louis, Mo., USA). All other chemicals were purchased from Sinopharm Chemicals (Beijing, P. R. China). Recombinant human HER2/ErbB2/CD340 (676-1255) protein was purchased from Sino Biological Inc. (Beijing, China). QDB plate was manufactured by Yantai Zestern Biotechnique Co. Ltd at Yantai, China.

Ventana anti-HER2/neu(4B5) rabbit monoclonal primary antibody and anti-Human estrogen receptor (clone Sp1) were purchased from Roche Diagnostics GmbH. Rabbit anti-HER2 antibody (clone EP3) and Mouse anti-human Ki67 (clone MIB1) were purchased from ZSGB-BIO (Beijing, China). HRP labeled Donkey Anti-Rabbit IgG secondary antibody was purchased from Jackson Immunoresearch lab (Pike West Grove, Pa., USA).

Preparation of Cell and Tissue Lysates

For frozen tissues, about 150 mg tissues were cut from tissue biopsies, and processed in 300 μl lysis buffer (50 mM HEPES, 137 mM NaCl, 5 mM EDTA, 1 mM MgCl, 10 mM $Na_2P_2O_7$, 1% TritonX-100, 10% glycerol) with protease inhibitors (2 μg/ml Leupeptin, 2 μg/ml Aprotinin, 1 μg/ml pepstatin, 2 mM PMSF, 2 mM NaF) with a handheld tissue homogenizer for 30 s before they were centrifuged at 12000×g for 5 mins. The supernatants were collected for immunoblot analysis. The total protein concentration was measured using Pierce BCA protein assay kit in accordance to the manufacturer's instructions. To prepare lysates from MCF-7 and BT-474 cells, cells were lysed in lysis buffer with protease inhibitors by pipetting up and down for 50 times. Supernatants were collected after centrifugation and the total protein concentration was determined by the BCA protein assay kit.

For Formalin fixed paraffin embedded (FFPE) blocks, two 2×15 μm slices were collected, de-paraffined and processed in 3000 lysis buffer (50 mM HEPES, 137 mM NaCl, 5 mM EDTA, 1 mM MgCl, 10 mM $Na_2P_2O_7$, 1% TritonX-100, 10% glycerol) with protease inhibitors (2 μg/ml Leupeptin, 2 μg/ml Aprotinin, 1 μg/ml pepstatin, 2 mM PMSF, 2 mM NaF) before they were centrifuged at 12000×g for 5 mins. The supernatants were collected for immunoblot analysis. The total protein concentration was measured using Pierce BCA protein assay kit in accordance to the manufacturer's instructions. To prepare lysates from MCF-7 and BT-474 cells, cells were lysed in lysis buffer with protease inhibitors by pipetting up and down for 50 times. Supernatants were collected after centrifugation and the total protein concentration was determined by the BCA protein assay kit.

Dot Blot Analysis

Purified her2 protein was serially diluted as indicated in the figure, and spotted on the a membrane together with total proteins extracted from FFPE slices. These samples were processed in a typical dot blot process until the image was captured using C-Digit Western blot scanner from Li-Cor. The image was converted into a number using ImageQuanti program from Li-Cor, and a protein standard curve was established to convert the images captures from patient samples into absolute biomarker levels.

QDB Analysis

The linear range of a specific antibody (EP3 or 4B5 clone for Her2; MIB1 for Ki67, SP1 for Estrogen receptor (ER)) was determined by using a pooled lysate from patients testing positive respectively for these biomarkers. The lysates were prepared first by mixing in equal amount tissue lysates prepared from 3 to 4 breast or stomach cancer tissues. The pooled lysates were serially diluted from 0-2 μg to define the linear range of QDB analysis. A protein standard either obtained commercially or expressed and purified in the company was also serially diluted from 0-500 pg, and used to define the linear range of QDB analysis.

The samples were applied onto the QDB plates at 20/unit in triplicate, and were processed as described previous[15]. A primary antibody was used for primary antibody incubation at 100 ul/well overnight at 4° C. and a donkey anti-rabbit or donkey anti-mouse secondary antibody was incubated with the plate for 4 hours at room temperature. The plates were briefly rinsed twice with TBST, and washed 5×10 mins before they were inserted into a white 96-well plate pre-filled with ECL solution prepared according to the manufacturer's instruction at 1000/well for 3 mins. The chemiluminescence signal from individual well of the plate was quantified by using the Tecan Infiniti 200 pro Microplate reader with the option "plate with cover".

A linear regression formula was established using serially diluted protein standard respectively. The formula was used to calculate the total HER2 level in each breast cancer tissue samples, and the results were corrected by total protein amount measured by the BCA protein determination kit. To ensure the consistency of the experiments, two cell lysates prepared from BT474 and MCF7 were used as positive and negative controls. The lysates were prepared in small aliquots. The absolute biomarker levels from two cell lysates were measured with QDB analysis and documented prior to being included and processed as regular samples in all the QDB experiments performed. Samples with chemiluminescence reading less than 2 fold over blank were regarded as non-detectable, and entered as 0 for data analysis. The final result was further corrected by the percentage of the purity of the recombinant HER2 protein.

Statistical Analysis

Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease, therapeutic effectiveness of a drug, and the like. Biomarkers are thus analytes in assays that facilitate diagnosis and the like.

All the data were presented as Mean±Standard Deviation (SD). The difference between individual groups was calculated using Microsoft Excel using unpaired two-tailed Student's t tests. P value <0.05 was considered statistically significant. Receiver operating characteristic (ROC) curves were generated using the GraphPad Prism software version 7.0 (GraphPad Software Inc., USA), as indicated in the figure legend.

EXAMPLES

Example 1 Teaches how to Measure Absolute Her2 Level in FFPE Specimen Using Dot Blot Analysis In 1A, recombinant Her2 protein was serially diluted and spotted onto a membrane together with four patient samples extracted from FFPE blocks.

The spotted protein standards and patient samples on the membrane was processed in dot blot analysis using EP3 clone for Her2 protein, and the image was captured using C-Digit Western blot scanner from Li-Cor, as shown in FIGS. 1A and 1B.

The image in FIG. 1A was converted into numbers using ImageQuant software from Li-Cor, and these numbers were used to establish a protein standard curve, as shown in FIG. 1C.

The images from 4 patient samples were also converted into number using the same computer software, and the numbers were converted into absolute Her2 level based on the protein standard curve established in section [0098].

Figure 2E:
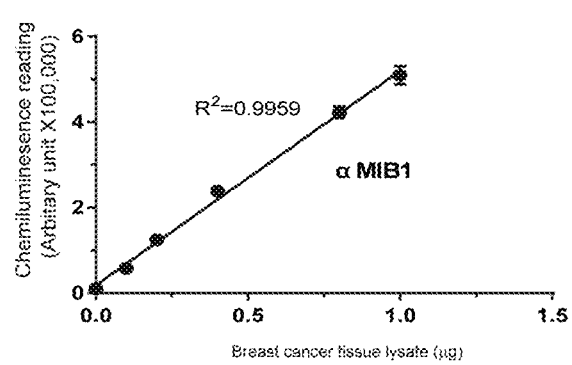
Figure 2B:
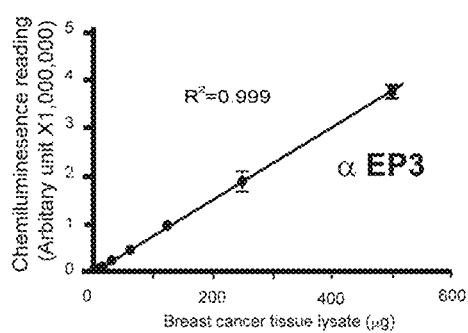
Figure 2F:
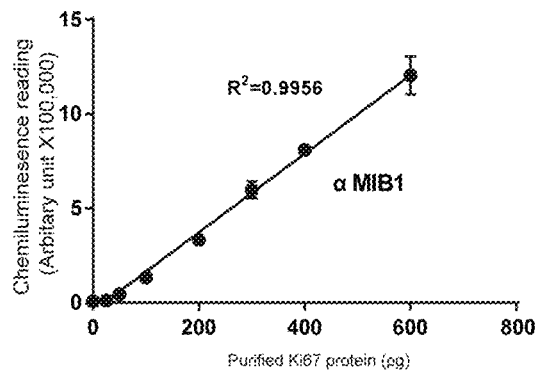
Figure 2C:
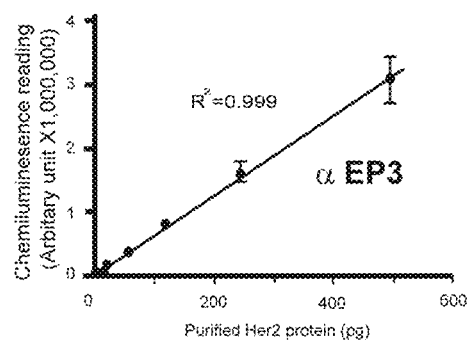
Figure 2G:
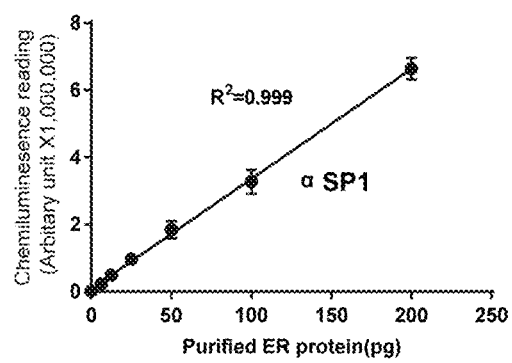
Figure 2D:
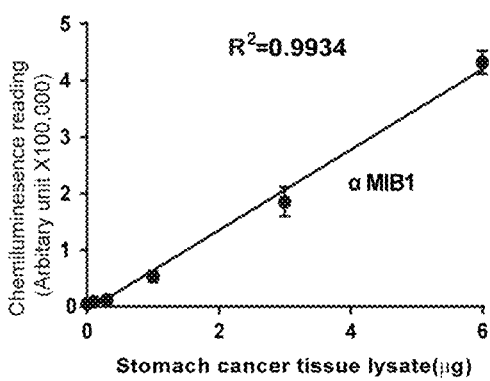
Figure 2H:
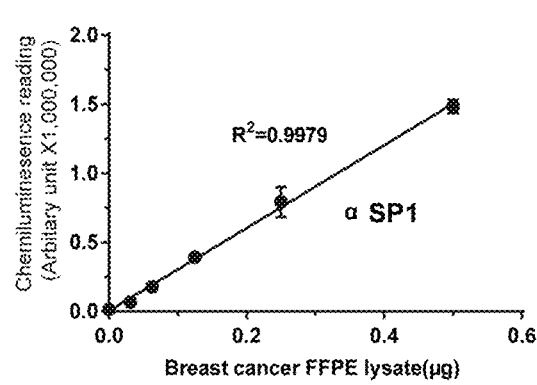

FIGS. 2A-2H teach how to define the linear range of the QDB analysis using a specific antibody. FIG. 2A showed the linear range of QDB analysis of frozen breast cancer tissues using Her2-EP3 antibody; FIG. 2B showed the linear range of QDB analysis of FFPE slices using Her2-EP3 antibody; FIG. 2C showed the linear range of QDB analysis of a recombinant Her2 protein, FIG. 2D showed the linear range of QDB analysis of frozen stomach cancer tissue using MIB1 antibody, FIG. 2E showed the linear range of QDB analysis of FFPE slices using MIB1 antibody against Ki67, 2F showed the linear range of QDB analysis of a recombinant fragment of Ki67 protein using MIB1 antibody, FIG. 2G showed the linear range of QDB analysis of a recombinant fragment of Estrogen Receptor (ER) protein using SP1 antibody, and FIG. 2H showed the linear range of QDB analysis of FFPE slices using SP1 antibody against ER.

Figure 3A:
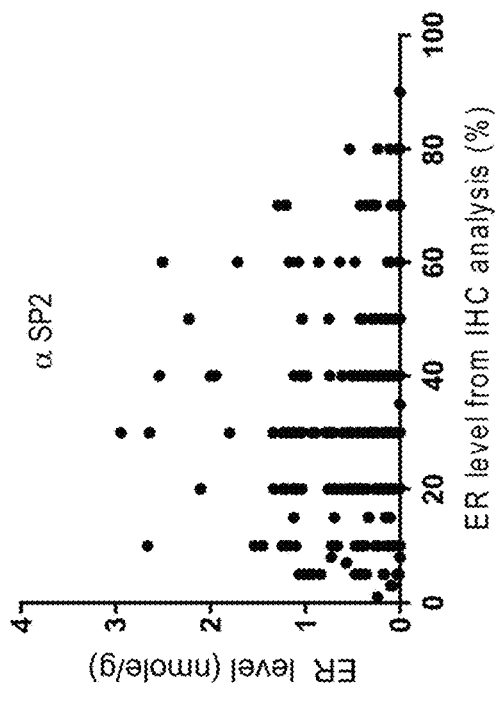
FIGS. 3A-3D show the absolute levels of Her2, Ki67, ER in breast cancer tissues extracted from FFPE specimens, measured with QDB analysis, and the absolute Her2 levels in frozen stomach tissues. The result was further grouped based on their IHC results respectively.
Figure 3C:
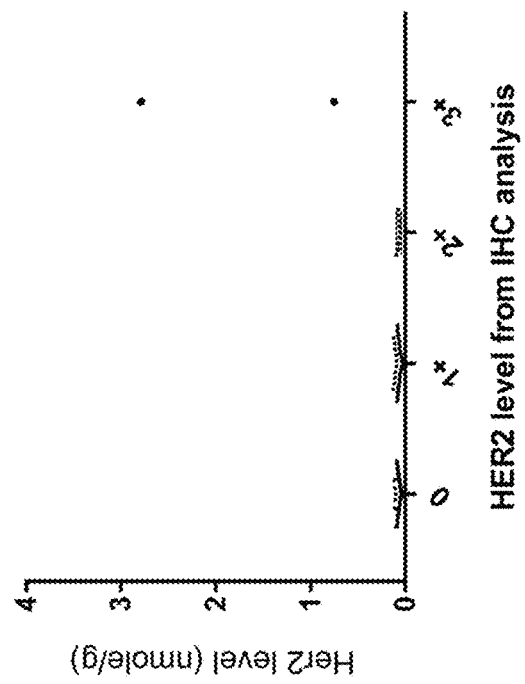
Figure 3B:
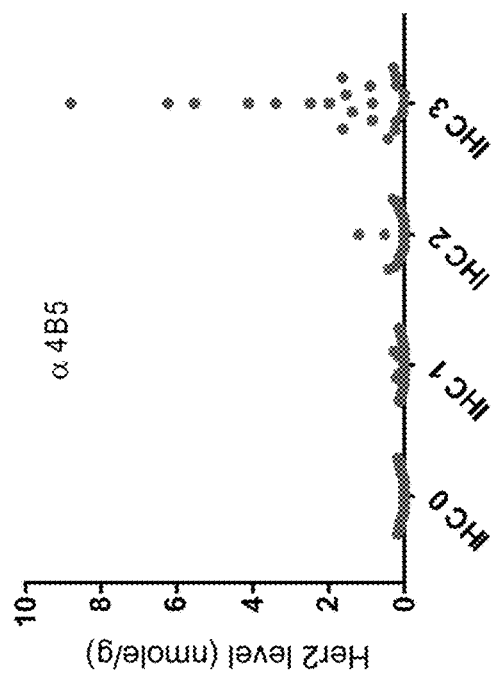
Figure 3D:
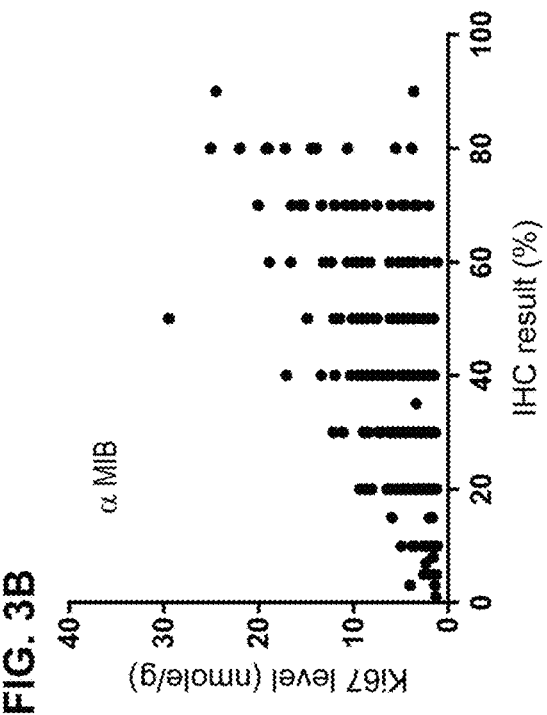

FIGS. 3A-3D show the absolute level of Her2 (A), Ki67 (B) and ER (C) in breast cancer tissues using Her2-4B5, MIB1 and SP2 antibodies respectively. In FIG. 3D, the Her2 absolute levels in frozen stomach cancer were measured using Her2-EP3 antibody. The results were average of three independent experiments in triplicate, and were grouped based on their IHC scores.

Figure 4A:
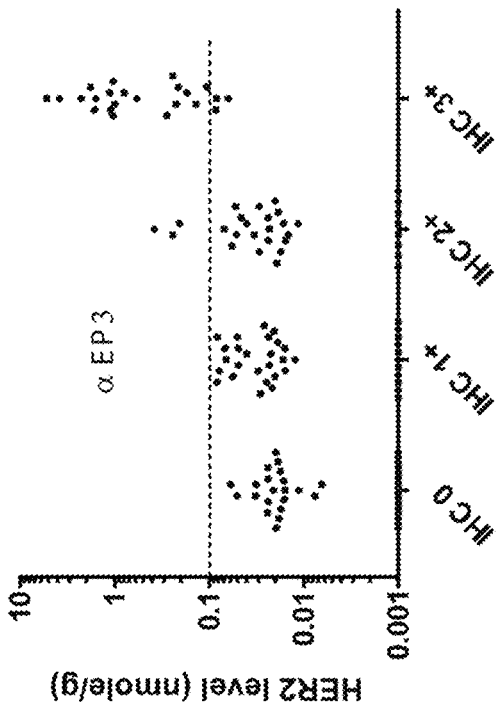
FIGS. 4A-4D show how to define a cutoff value to convert continuous data into categorized results based on Her2 absolute levels measured with QDB analysis, and the corresponding IHC results, obtained from local hospital.
Figure 4B:
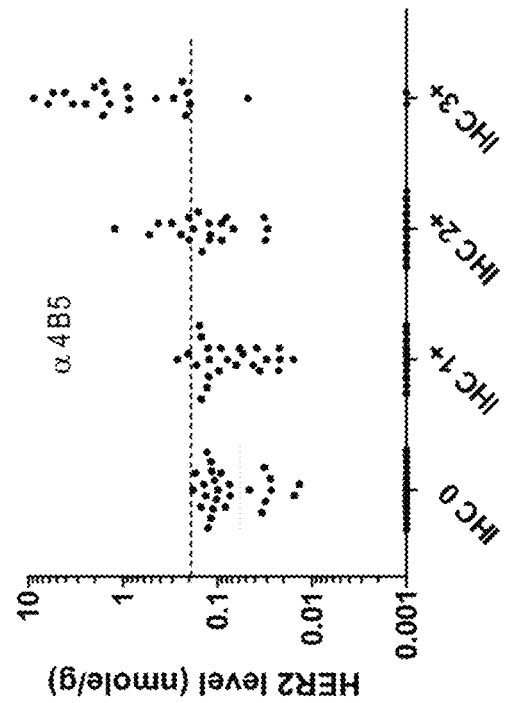
Figure 4C:
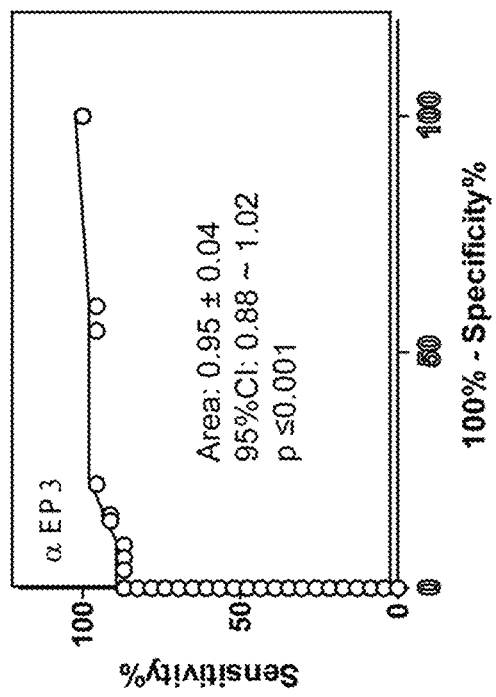
Figure 4D:
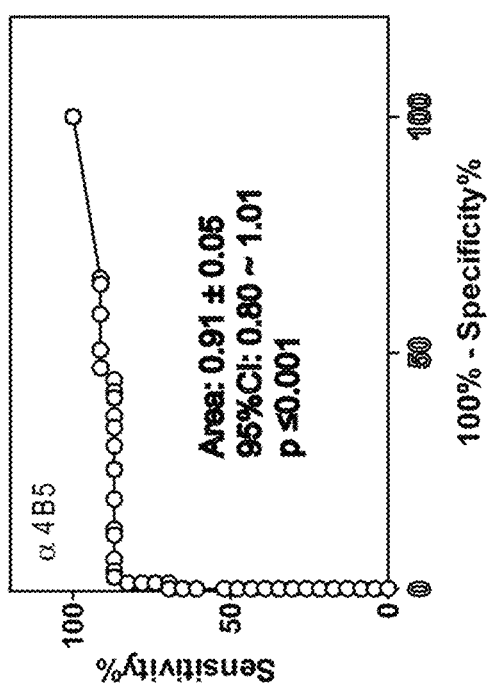

FIGS. 4A-4D show how to convert a QDB result into a categorized result using Receiving Operative Characteristic (ROC) analysis. The results from QDB analysis were separated into negative and positive groups based on their IHC results, and these two groups of numbers were used to calculate the cutoff value with promising specificity and sensitivity. FIGS. 4A and 4B showed ROC curves of QDB results from HER2-EP3 and HER2-4B5 antibodies respectively. FIGS. 4C and 4D showed how to separate QDB results into negative and positive groups based on the suggested cutoff value from ROC analysis.

Figure 5:
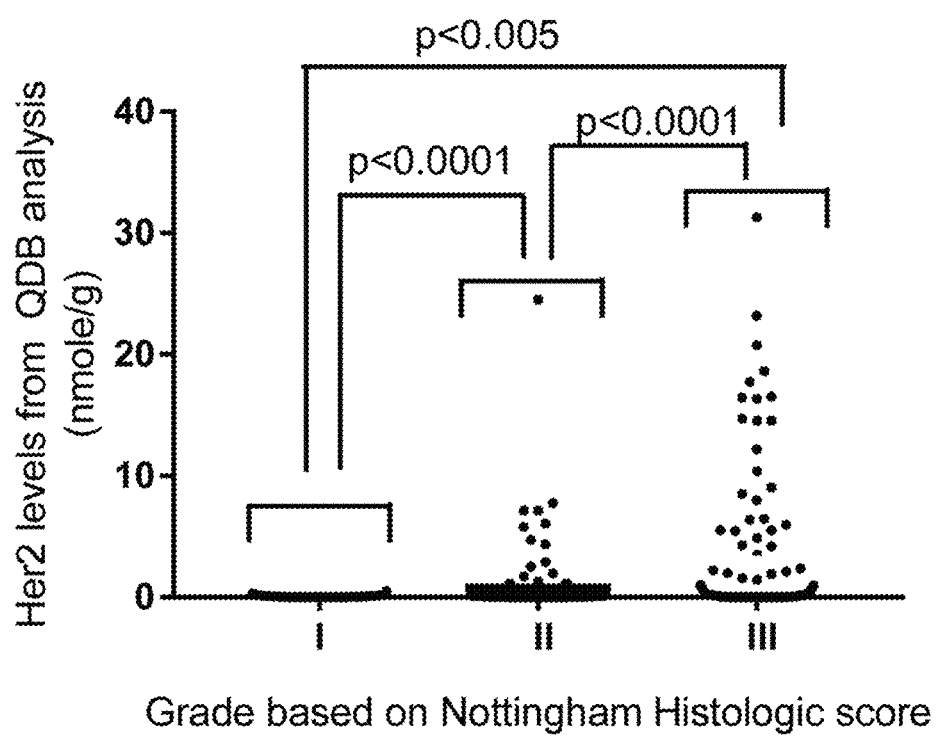
FIG. 5 shows how to analyze the clinical data using absolute value of a biomarker. In this case, the potential link between Her2 absolute level and the histologic grade of breast cancer patients was investigated.

In FIG. 5, the absolute Her2 levels from 263 FFPE specimens were measured, and plotted as a group based on the provided histologic grade judged by local hospital based on Nottingham histologic scores. There were 34 samples in group I, 125 samples with grade II, and 104 samples in grade III group. The averages of three grades were 0.08, 0.73, and 3.15 nmole/g. The her2 level were significantly higher with patients in Grade III group than those from Grade I and Grade II group, and absolute her2 level was significantly higher among patients in Grade II group than those in Grade I group. This result cannot be achieved with the current prevailing categorized system with both IHC and FISH analyses.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

It is believed that the following claims particularly point out certain embodiments or combined thereof that are directed to one of the disclosed inventions and are novel and non-obvious. Inventions embodied in other combinations or subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A method for quantitative analysis of a sample, comprising:
    (a) providing a singular marker representative of one or more features of the sample, the sample being a formalin-fixed paraffin-embedded (FFPE) tissue sample having a population of individual units of the marker;
    (b) extracting markers from the tissue sample and measuring the marker with quantitative dot blot analysis (QDB), wherein the quantitation result is an absolute amount of the marker's population of individual units in the sample, normalized by the protein weight, and the marker standard curve is established to convert signals captured into absolute marker level; and (c) obtaining a determination of the one or more features of the sample based on the absolute quantitation result of the marker.

2. The method of claim 1, wherein the step (b) comprises:
    (b1) incubating the sample with a solution comprising a binding agent, wherein:
    the binding agent is capable of specifically binding to an individual unit of the marker, and
    the binding agent is capable of being quantified by the dot blot analysis; and
    (b2) measuring the marker through QDB analysis of the binding agent.

3. The method of claim 2, wherein the marker is a protein marker and the binding agent is an antibody.

4. The method of claim 3, wherein the antibody is an analyte specific regent (ASR) antibody.

5. The method of claim 3, wherein the antibody is an in vitro diagnostics (IVD) antibody.

6. The method of claim 3, wherein the antibody is capable of being assayed in immunohistochemistry.

7. The method of claim 1, wherein the sample is a biopsy tissue from a subject.

8. The method of claim 7, wherein the subject is a cancer patient.

9. The method of claim 8, further comprising (d) evaluating the patient based on the quantitation result of the marker.

10. The method of claim 9, wherein, in step (d), evaluating the patient comprises diagnosis and prognosis of a cancer for the patient.

11. The method of claim 10, wherein the diagnosis and prognosis of a cancer comprises disease-free survival, overall survival, hazard ratio, or treatment prediction for the cancer.

12. A method for diagnosing cancer in a patient, comprising:

(a) obtaining a biopsy sample from the patient;

(b) measuring a marker in the biopsy sample with QDB analysis, wherein the measured result is an absolute amount of the marker in the biopsy sample normalized by protein weight and the marker standard curve is established to convert signals captured into absolute level;

(c) comparing the quantitation result of the marker with that of a reference profile stored in a reference database; wherein the reference profile database is obtained by measuring the biomarker from samples of a known cancer diagnosis using the same quantitative measurement of QDB analysis of step (b); and (d) identifying a reference profile in the reference database that has the best match and administering therapeutics to said patient.

13. The method of claim 12, wherein the cancer is a solid tumor cancer.

* * * * *